US008686181B2

(12) United States Patent
Knebel et al.

(10) Patent No.: US 8,686,181 B2
(45) Date of Patent: Apr. 1, 2014

(54) METHOD FOR PRODUCING ETHYLENE GLYCOL DIMETHACRYLATE

(75) Inventors: Joachim Knebel, Alsbach-Haehnlein (DE); Thorben Schuetz, Seeheim-Jugenheim (DE); Guido Protzmann, Bensheim (DE); Harald Trauthwein, Buerstadt (DE); Guenther Lauster, Worms (DE); Thomas Kehr, Muehltal (DE); Gerhard Koelbl, Gernsheim (DE); Guenter Westhaeuser, Guntersblum (DE)

(73) Assignee: Evonik Roehm GmbH, Darmstadt (DE)

( * ) Notice: Subject to any disclaimer, the term of this patent is extended or adjusted under 35 U.S.C. 154(b) by 994 days.

(21) Appl. No.: 12/667,538

(22) PCT Filed: May 8, 2008

(86) PCT No.: PCT/EP2008/055668
§ 371 (c)(1),
(2), (4) Date: May 12, 2010

(87) PCT Pub. No.: WO2009/003745
PCT Pub. Date: Jan. 8, 2009

(65) Prior Publication Data
US 2013/0172598 A1 Jul. 4, 2013

(30) Foreign Application Priority Data
Jul. 5, 2007 (DE) .......................... 10 2007 031 473

(51) Int. Cl.
*C07C 67/03* (2006.01)
(52) U.S. Cl.
USPC ....................................................... 560/217
(58) Field of Classification Search
CPC ...................................................... C07C 67/03
See application file for complete search history.

(56) References Cited

U.S. PATENT DOCUMENTS

| 4,672,105 A | 6/1987 | Schlosser et al. |
| 4,791,221 A | 12/1988 | Gabillet |
| 5,362,904 A | 11/1994 | Kearns |
| 6,541,658 B2* | 4/2003 | Knebel et al. ................. 560/217 |
| 7,521,578 B2 | 4/2009 | Schmitt et al. |
| 7,528,278 B2* | 5/2009 | Benderly et al. .............. 560/217 |
| 2002/0111511 A1 | 8/2002 | Knebel et al. |
| 2008/0194861 A1 | 8/2008 | Schmitt et al. |

FOREIGN PATENT DOCUMENTS

| AT | E 46 317 B | 2/1987 |
| DE | 101 06 642 A1 | 8/2002 |
| DE | 10 2005 044 250 A1 | 3/2007 |
| EP | 0 534 666 | 3/1993 |
| EP | 1 231 202 | 8/2002 |
| JP | 61-56155 A | 3/1986 |
| WO | 2007 031384 | 3/2007 |

OTHER PUBLICATIONS

U.S. Appl. No. 12/667,604, filed Jan. 4, 2010, Schmitt, et al.
U.S. Appl. No. 12/667,822, filed Jan. 5, 2010, Knebel, et al.
U.S. Appl. No. 12/667,599, filed Jan. 4, 2010, Protzmann, et al.
Office Action issued Mar. 27, 2013, in Japanese Patent Application No. 2010-513808 (German-language translation only).
Office Action issued Jan. 5, 2011, in Chinese Patent Application No. 200710148929.9 (with English-language translation).
German Search Report issued Feb. 22, 2008, in Patent Application No. 10 2007 031 473.8 (with English Translation of Categories of Cited Documents).
Combined Office Action and Search Report issued Jul. 15, 2013 in Taiwanese Patent Application No. 097124962 submitting English translation only.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to a process for preparing ethylene glycol dimethacrylate, which comprises transesterification of ethylene glycol with an ester of methacrylic acid in the presence of catalysts, wherein a combination comprising lithium amide ($LiNH_2$) and lithium chloride (LiCl) is used as catalyst. The process of the invention makes it possible to prepare ethylene glycol dimethacrylate particularly inexpensively and in a very high purity.

26 Claims, No Drawings

METHOD FOR PRODUCING ETHYLENE GLYCOL DIMETHACRYLATE

The invention relates to a process for preparing ethylene glycol dimethacrylate.

Ethylene glycol dimethacrylate is a widely known and used monomer which is employed, in particular, for crosslinking. Accordingly, a variety of methods of obtaining this compound is known. They include, in particular, transesterification reactions in which methyl methacrylate is reacted with ethylene glycol. To improve the yield and the selectivity of the reaction, various catalysts can be used.

For example, the publication DE 28 05 702 describes the preparation of esters of unsaturated carboxylic acids. To catalyse the reactions described, it is possible to use, in particular, compounds which contain zirconium and/or calcium. A particularly suitable catalyst is, in particular, zirconium acetylacetonate. The reactions lead to high yields of about 97%, based on the alcohol used. However, they have the disadvantage that the catalyst can be separated off from the reaction mixture only with great difficulty and, in particular, is inactive toward ethylene glycol as reactant.

Although a process for separating off this catalyst is disclosed in DE 199 40 622, the process is relatively expensive to carry out.

More, it is possible to use acids or bases to catalyse the transesterification. Such reactions are disclosed, for example, in CN 1355161, DE 34 23 443 or EP-A-0 534 666. However, when these catalysts are used, secondary reactions such as the Michael addition which decreases both the purity of the desired ethylene glycol dimethacrylate and the yield have to be expected. Basic catalysts include, in particular, lithium amide as is disclosed, for example, in the publications DE 34 23 443, CA 795814 and U.S. Pat. No. 6,194,530. However, the combination of lithium amide with further catalysts is not described.

In view of the prior art, it was an object of the present invention to provide a process for preparing ethylene glycol dimethacrylate, in which the product can be obtained very inexpensively. Furthermore, the ethylene glycol dimethacrylate obtained should contain only very small amounts of by-products and catalyst residues.

A further object of the invention was to invent a process in which ethylene glycol dimethacrylate can be obtained very selectively.

In addition, it was an object of the present invention to provide processes for preparing ethylene glycol dimethacrylate which can be carried out simply and inexpensively. Here, the product should be obtained in very high yields and, viewed overall, with a low energy consumption.

These objects and also further objects which have not been explicitly mentioned here but can readily be derived or deduced from the relationships discussed here are achieved by a process having all features of Claim 1. Advantageous modifications of the process of the invention are protected in the dependent claims which refer back to Claim 1.

The present invention accordingly provides a process for preparing ethylene glycol dimethacrylate, which comprises transesterification of ethylene glycol with an ester of methacrylic acid in the presence of catalysts, wherein a combination comprising lithium amide and lithium chloride is used as catalyst.

This has made it possible to provide, in an unforeseeable manner, a process for preparing ethylene glycol dimethacrylate in which the product is obtained very inexpensively. The product obtained surprisingly contains only small amounts of by-products and catalyst residues.

Furthermore, the process of the invention makes a particularly selective preparation of ethylene glycol dimethacrylate possible.

In addition, the process of the invention can be carried out simply and inexpensively and the product can be obtained in high yields and, viewed overall, with a low energy consumption.

According to the invention, ethylene glycol dimethacrylate (1,2-ethanediyl di-2-methylpropenoate) having the CAS number 97-90-5 is prepared.

According to the invention, ethylene glycol (1,2-ethanediol) is used to prepare ethylene glycol dimethacrylate. This compound is commercially available from BASF, Dow or Shell and has the CAS number 107-21-1.

According to the present invention, ethylene glycol is reacted with an ester of methacrylic acid. Particularly suitable methacrylates are formed, in particular, by alcohols having from 1 to 4 carbon atoms. These include, in particular, methanol, ethanol, n-propanol, isopropanol, n-butanol and tert-butanol. In particular, particular preference is given to using ethyl methacrylate or methyl methacrylate, with methyl methacrylate being very particularly preferred.

The weight ratio of ethylene glycol to the ester of methacrylic acid is preferably in the range from 1:2 to 1:20, particularly preferably from 1:5 to 1:15 and very particularly preferably in the range from 1:6 to 1:10.

According to the invention, a combination comprising lithium amide ($LiNH_2$) and lithium chloride (LiCl) is used for catalysing the present transesterification. Lithium amide has the CAS number 7782-89-0, and lithium chloride has the CAS number 7447-41-8.

The weight ratio of lithium amide to lithium chloride can, depending on the reaction conditions, be within a wide range. This ratio can advantageously be, for example, in the range from 20:1 to 1:20, particularly preferably in the range from 5:1 to 1:1.

The amount of catalyst used can be within a wide range. However, processes in which the proportion of catalyst, based on the weight of the ethylene glycol used, is in the range from 0.05 to 8% by weight, preferably in the range from 0.01 to 5% by weight and particularly preferably in the range from 0.1 to 1% by weight, are of particular interest.

The total amount of catalyst used can be added to the reaction mixture at the beginning of the reaction. In a particularly advantageous modification, part of the catalyst, preferably part of the lithium amide, can be added to the reaction mixture during the course of the reaction. Preference is given to adding further catalyst to the reaction mixture after a conversion in the range from 20 to 80%, particularly preferably in the range from 30% to 60%, based on the weight of the ethylene glycol used. In particular, processes in which at least 10% by weight, particularly preferably at least 20% by weight, of the lithium amide is added to the reaction mixture during the reaction are of particular interest.

The reaction can be carried out under superatmospheric or subatmospheric pressure. In a particularly advantageous modification of the present invention, the transesterification can be carried out at a pressure in the range from 200 to 2000 mbar, particularly preferably in the range from 500 to 1300 mbar.

The reaction temperature can, especially as a function of the pressure, likewise be within a wide range. In a particular embodiment of the present invention, the reaction is preferably carried out at a temperature in the range from 60° C. to 150° C., particularly preferably in the range from 70° C. to 140° C. and very particularly preferably from 90 to 130° C.

Particular advantages can surprisingly be achieved if the temperature at which the reaction occurs is increased during the course of the reaction. In this preferred modification of the process of the invention, the temperature at the beginning of the reaction, in particular up to a conversion of 80%, preferably up to a conversion of 70%, based on the weight of the ethylene glycol used, can preferably be in the range from 90° C. to 110° C. and that towards the end of the reaction, in particular after a conversion of 80%, preferably after a conversion of 90%, based on the weight of the ethylene glycol used, can be in the range from 115° C. to 130° C.

The transesterification can be carried out either continuously or batchwise. The process of the invention can be carried out in bulk, i.e. without use of a further solvent. If desired, an inert solvent can also be used. Such solvents include, inter alia, benzene, toluene, n-hexane, cyclohexane and methyl isobutyl ketone (MIBK) and methyl ethyl ketone (MEK).

In a particularly advantageous variant of the transesterification of the invention, all components, for example the ethylene glycol, the methacrylic ester and the catalyst, are mixed, after which this reaction mixture is heated to boiling. The alcohol liberated, for example methanol or ethanol, can subsequently be removed from the reaction mixture by distillation, if appropriate as an azeotrope with methyl methacrylate or ethyl methacrylate.

The reaction times depend, inter alia, on the parameters selected, for example pressure and temperature. However, they are generally in the range from 1 to 24 hours, preferably from 5 to 20 hours and very particularly preferably from 6 to 12 hours. In the case of continuous processes, the residence times are generally in the range from 0.5 to 24 hours, preferably from 1 to 12 hours and very particularly preferably from 2 to 3 hours. A person skilled in the art can find further information on the reaction times in the examples attached.

The reaction can preferably take place with stirring, with the stirring rate particularly preferably being in the range from 50 to 2000 rpm, very particularly preferably in the range from 100 to 500 rpm.

The pH can be within a wide range. The reaction can advantageously be carried out at a pH in the range from 8 to 14, preferably from 9 to 13.

To prevent undesirable polymerization of the methacrylates, polymerization inhibitors can be used in the reaction. These compounds, for example hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidin-1-oxyl, p-phenylenediamine, methylene blue or sterically hindered phenols, are widely known in the art. These compounds can be used individually or in the form of mixtures and are generally commercially available. The mode of action of the stabilizers is usually that they act as free-radical scavengers for the free radicals occurring in the polymerization. Further details may be found in the relevant specialist literature, in particular Römpp-Lexikon Chemie; editor: J. Falbe, M. Regitz; Stuttgart, N.Y.; 10th Edition (1996); key word "Antioxidantien", and the references cited here.

Preference is given to using, in particular, amines as polymerization inhibitor. Particularly surprising advantages can be achieved when using N,N'-(diphenyl)-p-phenylenediamine. Based on the weight of the total reaction mixture, the proportion of inhibitors, either individually or as a mixture, can generally be 0.01-0.5% (wt/wt).

These polymerization inhibitors can be added to the reaction mixture before or at the beginning of the reaction. Furthermore, small proportions of the polymerization inhibitors employed can be introduced during the transesterification. Processes in which part of the polymerization inhibitor is added via the column runback are of particular interest here. It is particularly advantageous to use, inter alia, mixtures containing methyl methacrylate, hydroquinone monomethyl ether and 4-hydroxy-2,2,6,6-tetramethylpiperidin-1-oxyl. This measure makes it possible, in particular, to avoid undesirable polymerization within the distillation column.

Furthermore, oxygen can be used for the inhibition. This can be used, for example, in the form of air, with the amounts introduced advantageously being such that the content in the gas phase above the reaction mixture remains below the explosive limit. Amounts of air in the range from 0.05 to 0.5 l per hour and mole of ethylene glycol are particularly preferred here. In batch processes, this amount can be based on the amount of ethylene glycol originally used. In the case of continuous processes, this amount can be based on the amount of ethylene glycol fed in. It is likewise possible to use inert gas/oxygen mixtures, e.g. nitrogen/oxygen or argon/oxygen mixtures.

In a particular embodiment of the present invention, a combination of oxygen with at least one amine, preferably N,N'-(diphenyl)-p-phenylenediamine, can be used for inhibition.

In an advantageous embodiment of the present invention, the alcohol liberated from the methacrylate used, for example methanol and/or ethanol, can be separated off by distillation. Here, a mixture containing, for example, methyl methacrylate and methanol can advantageously be separated off. Surprisingly, part of the mixture which has been separated off can advantageously be recirculated to the next batch. In this modification, the proportion which can be recirculated of the mixture which has been separated off can be obtained at the end of the reaction, in particular after a conversion of 80%, preferably after a conversion of 90%, of the ethylene glycol used. For example, the proportion of the recirculated mixture at the beginning of the next batch can be in the range from 10 to 50%, based on the total weight of methacrylic ester to be transesterified.

Batch processes in which methyl methacrylate is added during the transesterification are, inter alia, of particular interest. This embodiment is advantageous, for example, if methyl methacrylate is removed together with methanol from the reaction mixture. The weight ratio of the amount of methyl methacrylate added during the transesterification to the amount of methanol/methyl methacrylate mixture separated off can preferably be in the range from 2:1 to 1:2.

In the case of batch processes, excess starting material, in particular the unreacted ester of methacrylic acid, can be separated off by distillation towards the end of the reaction. This too can be reused without further purification in the next batch.

The methanol- or ethanol-rich distillate obtained at the beginning of the reaction can likewise be recycled, for example by introduction into a coupled plant for preparing the methacrylate ester to be transesterified.

A suitable plant for carrying out the present transesterification can comprise, for example, a stirred tank reactor provided with agitator, steam heating, distillation column and condenser. Such plants are known per se and are described, for example, in Ullmanns Encyclopedia of Industrial Chemistry (6th Edition), Verlag Wiley-VCH, Weinheim 2003, Volume 10, page 647. The size of the plant depends on the amount of ethylene glycol dimethacrylate to be prepared, with the present process being able to be carried out either on a laboratory scale or on an industrial scale. According to a particular aspect, the stirred tank reactor can accordingly have a tank volume in the range from 1 $m^3$ to 30 $m^3$, preferably from 3 m³ to 20 m³. The agitator of the reactor tank can, in particular, be configured in the form of an anchor stirrer, impeller, paddle stirrer or Inter-MIG stirrer.

The task of the distillation column is to ensure that a methanol- or ethanol-rich azeotrope is taken off in order to minimize the losses of starting ester which is inevitably discharged. The distillation column can have one, two or more separation stages. The number of separation stages is the number of trays in the case of a tray column or the number of theoretical plates in the case of a column containing ordered packing or random packing elements. Examples of trays in a multistage distillation column are bubblecap trays, sieve trays, tunnel trays, valve trays, slotted trays, sieve-slotted trays, sieve-bubblecap trays, nozzle trays, centrifugal trays, examples of random packing elements in a multistage distillation column are Raschig rings, Lessing rings, Pall rings, Berl saddles, Intalox saddles and examples of ordered packing in a multistage distillation column are Mellapak (Sulzer), Rombopak (Kühni), Montz-Pak (Montz). Conversion-dependent adaptation of the reflux ratio enables, for example when using methyl methacrylate, a proportion of methanol in the distillate which is above 60% to be obtained over a wide conversion range.

Suitable condensers which can be present in the plant for carrying out the present transesterification include, inter alia, plate heat exchangers and shell-and-tube heat exchangers.

After the reaction is complete, the ethylene glycol dimethacrylate obtained frequently meets the exacting requirements indicated above, so that further purification is frequently not necessary. To increase the quality further and, in particular, to separate off the catalyst, the mixture obtained can be purified by known methods.

In an embodiment of the process of the invention, the product mixture obtained can be purified by means of filtration processes. These processes are known from the prior art (W. Gösele, Chr. Alt in Ullmann's Encyclopedia of Industrial Chemistry, (6th Edition), Verlag Wiley-VCH, Weinheim 2003, Volume 13, pages 731 and 746), which can be carried out using customary filtration aids such as aluminium silicate (Perlite). For example, it is possible to use, inter alia, continuously operable filters for a washcoat filtration or candle filters.

A further improvement in the quality of the product can be achieved, for example, by distillation of the filtrate obtained. Owing to the tendency of the monomer to polymerize, distillation processes in which the thermal stress on the substance to be distilled is minimized are advisable. Apparatuses in which the monomer is continuously vaporized from a thin layer, e.g. falling film evaporators and evaporators having a rotating wiper system, are well suited. Short path evaporators can also be used. Such apparatuses are known (Ullmanns Encyclopedia of Industrial Chemistry (6th Edition), Verlag Wiley-VCH, Weinheim 2003, Volume 36, page 505). Thus, for example, a continuous evaporator having a rotating wiper system and a superposed column can be used. The distillation can, for example, be carried out at a pressure in the range from 1 to 40 mbar and an evaporator temperature of from 120° C. to 150° C.

The present invention is illustrated below with the aid of examples and comparative examples, without this constituting a restriction.

EXAMPLE 1

444 kg of ethylene glycol, 3018 kg of methyl methacrylate (MMA), 0.167 kg of N,N'-(diphenyl)-p-phenylenediamine as inhibitor and a mixture of 0.5 kg of lithium amide and 0.25 kg of lithium chloride as catalyst are combined in a stirred tank reactor provided with agitator, steam heater, distillation column and condenser and stirred while passing in air. To stabilize the column, a total of 151 kg of MMA containing 0.24 kg of hydroquinone monomethyl ether and 0.016 kg of 4-hydroxy-2,2,6,6-tetramethylpiperidin-1-oxyl in dissolved form are introduced into the column runback. The reactor is heated to a temperature at the bottom of 97° C., with the column initially being operated with total reflux (about 15 minutes). As soon as the temperature at the top of the column drops to below 70° C., the methanol/MMA mixture is taken off at a reflux ratio of 2:1. The MMA stock in the reactor is supplemented by metered addition of equal parts of MMA per part of methanol/MMA mixture taken off. A total of 1320 kg of MMA are thus introduced over a period of 5 hours. After 450 l of methanol/MMA mixture has been taken off, another 0.5 kg of lithium amide is added. Over a period of 8 hours, the reflux ratio is raised to 1.1:1 as a function of the decreasing methanol formation. At a temperature at the bottom of 130° C., the reaction is complete and excess MMA is taken off under reduced pressure, with the pressure gradually being reduced to 100 mbar. When no more MMA distills off, the vacuum is broken. The contents of the tank, comprising the catalyst-containing ethylene glycol dimethacrylate, are admixed with 10 kg of aluminium silicate (Perlite) as filter aid and freed of catalyst by washcoat filtration or with the aid of a candle filter.

This gives 1415 kg of crude ester having the following composition (determined by gas chromatography):
Ethylene glycol dimethacrylate: 90%
Ethylene glycol monomethacrylate: 2.1%
MMA: 0.9%
Methacryloyloxyethyl 3-methoxyisobutyrate: 0.25%
Methacryloyloxyethyl 3-(methacryloyloxyethyl)isobutyrate 4.2%

The crude ester is fed at a rate of 300 kg/h into a continuous evaporator (area 3.5 m²) having a rotating wiper system and a superposed column which is operated without reflux at a pressure of 5 mbar and an evaporation temperature of 135° C. The output (280 kg/h) gives a total of 1320 kg of ethylene glycol dimethacrylate.

Composition (determined by gas chromatography):
Ethylene glycol dimethacrylate: 98.4%
Ethylene glycol monomethacrylate: 0.86%
MMA: 0.4%
Methacryloyloxyethyl 3-methoxyisobutyrate: 0.18%
Methacryloyloxyethyl 3-(methacryloyloxyethyl)isobutyrate: 0.14%

EXAMPLE 2

336 kg of ethylene glycol, 3112 kg of methyl methacrylate (MMA, consisting of 1600 kg of fresh MMA and 1512 kg of MMA from the vacuum phase of Example 1), 0.125 kg of N,N'-(diphenyl)-p-phenylenediamine as inhibitor and a mixture of 0.5 kg of lithium amide and 0.25 kg of lithium chloride as catalyst are combined in a stirred tank reactor provided with agitator, steam heater, distillation column and condenser and stirred while passing in air. To stabilize the column, a total of 151 kg of MMA containing 0.24 kg of hydroquinone monomethyl ether and 0.016 kg of 4-hydroxy-2,2,6,6-tetramethylpiperidin-1-oxyl in dissolved form are introduced into the column runback. The reactor is heated to a temperature at the bottom of 93° C., with the column initially being operated with total reflux (about 15 minutes). As soon as the temperature at the top of the column drops to below 70° C., the methanol/MMA mixture is taken off at a reflux ratio of 3:1. After 250 l of methanol/MMA mixture has been taken off, another 0.5 kg of lithium amide is added. After 8 hours, a temperature at the bottom of 130° C. is reached and the reaction is complete. Excess MMA is taken off under reduced pressure, with the pressure gradually being reduced to 100 mbar. When no more MMA distills off, the vacuum is broken. The contents of the tank, comprising the catalyst-containing ethylene glycol dimethacrylate, are admixed with 5 kg of aluminium silicate (Perlite) as filter aid and freed of catalyst by washcoat filtration or with the aid of a candle filter. This gives 1050 kg of crude ester having the following composition (determined by gas chromatography):

Ethylene glycol dimethacrylate: 96.8%
Ethylene glycol monomethacrylate: 0.31%
MMA: 0.75%
Methacryloyloxyethyl 3-methoxyisobutyrate: 0.035%
Methacryloyloxyethyl 3-(methacryloyloxyethyl)isobutyrate 0.5%

The crude ester is fed at a rate of 300 kg/h into a continuous evaporator (area 3.5 m$^2$) having a rotating wiper system and a superposed column which is operated without reflux at a pressure of 5 mbar and an evaporation temperature of 135° C. The output (280 kg/h) gives a total of 980 kg of ethylene glycol dimethacrylate.

Composition (determined by gas chromatography):
Ethylene glycol dimethacrylate: 98.8%
Ethylene glycol monomethacrylate: 0.68%
MMA: 0.32%
Methacryloyloxyethyl 3-methoxyisobutyrate: 0.05%
Methacryloyloxyethyl 3-(methacryloyloxyethyl)isobutyrate: 0.037%

EXAMPLE 3

1057 kg of ethylene glycol, 4290 kg of methyl methacrylate (MMA), 0.350 kg of N,N'-(diphenyl)-p-phenylenediamine and 0.16 kg of hydroquinone monomethyl ether and also 0.65 kg of a 5% strength solution of 4-hydroxy-2,2,6,6-tetramethylpiperidin-1-oxyl in MMA as inhibitors and a mixture of 1.45 kg of lithium amide and 0.7 kg of lithium chloride as catalyst are combined in a stirred tank reactor provided with agitator, steam heater, distillation column and condenser and stirred while passing in air. To stabilize the column, a total of 151 kg of MMA containing 0.36 kg of hydroquinone monomethyl ether and 0.019 kg of 4-hydroxy-2,2,6,6-tetramethylpiperidin-1-oxyl in dissolved form are introduced into the column runback. The reactor is heated to a temperature at the bottom of 97° C., with the column initially being operated with total reflux (about 15 minutes). As soon as the temperature at the top of the column drops to below 70° C., the methanol/MMA mixture is taken off at a reflux ratio of 2:1. The MMA stock in the reactor is supplemented by metered addition of equal parts of MMA per part of methanol/MMA mixture taken off. A total of 3442 kg of MMA are thus introduced over a period of 10 hours. After 800 l of methanol/MMA mixture has been taken off, another 1 kg of lithium amide is added, and another 0.5 kg is added after 2400 l of mixture has been taken off. At a temperature at the bottom of 130° C., the reaction is complete and excess MMA is taken off under reduced pressure, with the pressure gradually being reduced to 100 mbar. When no more MMA distills off, the vacuum is broken. The contents of the tank, comprising the catalyst-containing ethylene glycol dimethacrylate, are admixed with 10 kg of aluminium silicate (Perlite) as filter aid and freed of catalyst by washcoat filtration or with the aid of a candle filter. This gives 3370 kg of crude ester having the following composition (determined by gas chromatography):

Ethylene glycol dimethacrylate: 89%
Ethylene glycol monomethacrylate: 2.8%
MMA: 1%
Methacryloyloxyethyl 3-methoxyisobutyrate: 0.28%
Methacryloyloxyethyl 3-(methacryloyloxyethyl)isobutyrate 5%

The crude ester is fed at a rate of 400 kg/h into a continuous evaporator (area 3.5 m$^2$) having a rotating wiper system and a superposed column which is operated without reflux at a pressure of 5 mbar and an evaporation temperature of 135° C. The output (380 kg/h) gives a total of 3200 kg of ethylene glycol dimethacrylate.

Composition (determined by gas chromatography):
Ethylene glycol dimethacrylate: 97.1%
Ethylene glycol monomethacrylate: 1.7%
MMA: 0.27%
Methacryloyloxyethyl 3-methoxyisobutyrate: 0.38%
Methacryloyloxyethyl 3-(methacryloyloxyethyl)isobutyrate: 0.28%

COMPARATIVE EXAMPLE 1

Replacement of Lithium Amide by Potassium Methoxide 280 g of ethylene glycol, 1126 g of methyl methacrylate (MMA), 0.1 g of hydroquinone monomethyl ether and also 0.01 g of 4-hydroxy-2,2,6,6-tetramethylpiperidin-1-oxyl as inhibitors are combined in a 2 l round-bottom flask provided with agitator, electric heater, distillation column and condenser and stirred while passing in air. The mixture is heated to boiling and 77 g of an MMA/water mixture are distilled off. The apparatus is cooled to a temperature at the bottom of 74° C. and 77 g of pure MMA as supplement and a mixture of 2.73 g of potassium methoxide as 32% strength solution in methanol and 0.26 g of lithium chloride as catalyst are added. The reactor is heated to a temperature at the bottom of 87° C. As soon as the temperature at the top of the column drops to below 70° C., the methanol/MMA mixture is taken off at a reflux ratio of 5:1. The MMA stock in the reactor is supplemented by metered addition of equal parts of MMA per part of methanol/MMA mixture taken off. A total of 676 g of MMA are thus introduced over a period of 5 hours. After 2 hours, another 1.36 g of potassium methoxide as a 32% strength solution in methanol and 0.26 g of lithium chloride are added. At a temperature at the bottom of 120° C., the reaction is complete and excess MMA is taken off under reduced pressure, with the pressure gradually being reduced to 8-10 mbar. When no more MMA distills off, the vacuum is broken. The contents of the flask, comprising the catalyst-containing ethylene glycol dimethacrylate, are freed of the catalyst by pressure filtration using a filter layer from Seitz, type T120. This gives 731 kg of crude ester having the following composition (determined by gas chromatography):

Ethylene glycol dimethacrylate: 68.5%
Ethylene glycol monomethacrylate: 20.2%
MMA: 0.47%
Methacryloyloxyethyl 3-methoxyisobutyrate: 0.76%
Methacryloyloxyethyl 3-(methacryloyloxyethyl)isobutyrate 4%
Methacryloyloxyethyl 3-methylisobutyrate: 2%

COMPARATIVE EXAMPLE 2

Lithium Methoxide in Place of Lithium Amide 248 g of ethylene glycol, 1200 g of methyl methacrylate (MMA), 0.09 g of hydroquinone monomethyl ether and also 0.008 g of 4-hydroxy-2,2,6,6-tetramethylpiperidin-1-oxyl as inhibitors are combined in a 2 l round-bottom flask provided with agitator, electric heater, distillation column and condenser and stirred while passing in air. The mixture is heated to boiling and 67 g of an MMA/water mixture are distilled off. The apparatus is cooled to a temperature at the bottom of 85° C. and 67 g of pure MMA as supplement and 0.38 g of lithium methoxide as catalyst are added. The reactor is heated to a temperature at the bottom of 87° C. As soon as the temperature at the top of the column drops to below 70° C., the methanol/MMA mixture is taken off at a reflux ratio of 5:1. The MMA stock in the reactor is supplemented by metered addition of equal parts of MMA per part of methanol/MMA mixture taken off. A total of 601 g of MMA are thus introduced over a period of 4 hours. After 2.5 hours, another 0.38 g of lithium methoxide are added. At a temperature at the bottom of 125° C., the reaction is complete and excess MMA is taken off under reduced pressure, with the pressure gradually being reduced to 8-10 mbar. When no more MMA distills off, the vacuum is broken. The contents of the flask, comprising the catalyst-containing ethylene glycol dimethacrylate, are freed of the catalyst by pressure filtration using 4 g of Tonsil's 312 FF (montmorillonite from Süd Chemie) as adsorbent and a filter layer from Seitz, type T120. This gives 728 kg of crude ester having the following composition (determined by gas chromatography):

Ethylene glycol dimethacrylate: 83.7%
Ethylene glycol monomethacrylate: 3.2%
MMA: 0.66%
Methacryloyloxyethyl 3-methoxyisobutyrate: 1.9%
Methacryloyloxyethyl 3-(methacryloyloxyethyl)isobutyrate 5.8%
Methacryloyloxyethyl 3-methylisobutyrate: 2.7%

COMPARATIVE EXAMPLE 3

Sodium Methoxide in Place of Lithium Amide 280 g of ethylene glycol, 826 g of methyl methacrylate (MMA) and also 300 g of MMA from the vacuum offtake of Example 4 and 0.1 g of hydroquinone monomethyl ether as inhibitor are combined in a 2 l round-bottom flask provided with agitator, electric heater, distillation column and condenser and stirred while passing in air. The mixture is heated to boiling and 71 g of an MMA/water mixture are distilled off. The apparatus is cooled to a temperature at the bottom of 73° C. and 71 g of pure MMA as supplement and also 1.82 g of sodium methoxide in the form of a 30% strength solution in methanol and 0.85 g of lithium chloride as catalysts are added. The reactor is heated to a temperature at the bottom of 88° C. As soon as the temperature at the top of the column drops to below 70° C., the methanol/MMA mixture is taken off at a reflux ratio of 5:1. The MMA stock in the reactor is supplemented by metered addition of equal parts of MMA per part of methanol/MMA mixture taken off. A total of 450 g of MMA are thus introduced over a period of 3 hours. After 1 hour, another 0.91 g of sodium methoxide in the form of a 30% strength solution in methanol and 0.43 g of lithium chloride are added. At a temperature at the bottom of 128° C., the reaction is complete and excess MMA is taken off under reduced pressure, with the pressure gradually being reduced to 8-10 mbar. When no more MMA distills off, the vacuum is broken. The contents of the flask, comprising the catalyst-containing ethylene glycol dimethacrylate, are freed of the catalyst by pressure filtration using 4.5 g of Tonsil's 312 FF (montmorillonite from Süd Chemie) as adsorbent and a filter layer from Seitz, type T750. This gives 828 kg of crude ester having the following composition (determined by gas chromatography):

Ethylene glycol dimethacrylate: 85.4%
Ethylene glycol monomethacrylate: 1.1%
MMA: 0.05%
Methacryloyloxyethyl 3-methoxyisobutyrate: 1.3%
Methacryloyloxyethyl 3-(methacryloyloxyethyl)isobutyrate 8%
Methacryloyloxyethyl 3-methylisobutyrate: 2.4%

COMPARATIVE EXAMPLE 4

Lithium Nitrate in Place of Lithium Chloride 280 g of ethylene glycol and 1126 g of methyl methacrylate (MMA) and also 0.178 g of hydroquinone monomethyl ether and 0.01 g of 4-hydroxy-2,2,6,6-tetramethylpiperidin-1-oxyl as inhibitors are combined in a 2 l round-bottom flask provided with agitator, electric heater, distillation column and condenser and stirred while passing in air. The mixture is heated to boiling and 81 g of an MMA/water mixture are distilled off. The apparatus is cooled to a temperature at the bottom of 66° C. and 81 g of pure MMA as supplement and also 3.07 g of sodium methoxide in the form of a 30% strength solution in methanol and 1.17 g of lithium nitrate as catalysts are added. The reactor is heated to a temperature at the bottom of 87° C. As soon as the temperature at the top of the column drops to below 70° C., the methanol/MMA mixture is taken off at a reflux ratio of 5:1. The MMA stock in the reactor is supplemented by metered addition of equal parts of MMA per part of methanol/MMA mixture taken off. A total of 450 kg of MMA are thus introduced over a period of 5 hours. After 1.25 hours, another 1 g of sodium methoxide in the form of a 30% strength solution in methanol and 0.39 g of lithium nitrate are added. At a temperature at the bottom of 121° C., the reaction is complete and excess MMA is taken off under reduced pressure, with the pressure gradually being reduced to 5-6 mbar. When no more MMA distills off, the vacuum is broken. The contents of the flask, comprising the catalyst-containing ethylene glycol dimethacrylate, are freed of the catalyst by pressure filtration using a filter layer from Seitz, type T120. This gives 706 g of crude ester having the following composition (determined by gas chromatography):

Ethylene glycol dimethacrylate: 70%
Ethylene glycol monomethacrylate: 22.6%
MMA: 1%
Methacryloyloxyethyl 3-methoxyisobutyrate: 0.4%
Methacryloyloxyethyl 3-(methacryloyloxyethyl)isobutyrate 3.1%
Methacryloyloxyethyl 3-methylisobutyrate: 1.1%

The invention claimed is:
1. A process for preparing ethylene glycol dimethacrylate, comprising transesterifying ethylene glycol with an ester of methacrylic acid in a reaction mixture comprising at least one catalyst, wherein said catalyst comprises lithium amide (LiNH$_2$) and lithium chloride (LiCl).
2. The process according to claim 1, further comprising adding additional lithium amide to the reaction mixture during said transesterifying.
3. The process according to claim 1, wherein the weight ratio of lithium amide to lithium chloride is in the range of from 20:1 to 1:20.
4. The process according to claim 3, wherein the weight ratio of lithium amide to lithium chloride is in the range of from 5:1 to 1:1.

5. The process according to claim 1, wherein said transesterifying is carried out for a reaction time of from 5 to 20 hours.

6. The process according to claim 5, wherein said transesterifying is carried out for a reaction time of from 6 to 12 hours.

7. The process according to claim 1, wherein the ester of methacrylic acid is methyl methacrylate.

8. The process according to claim 1, wherein the ester of methacrylic acid is ethyl methacrylate.

9. The process according to claim 1, wherein the weight ratio of ethylene glycol to the ester of methacrylic acid is in the range of from 1:2 to 1:20.

10. The process according to claim 9, wherein the weight ratio of ethylene glycol to the ester of methacrylic acid is in the range of from 1:5 to 1:15.

11. The process according to claim 1, wherein said transesterifying is carried out at a pressure in the range of from 200 to 2000 mbar.

12. The process according to claim 1, wherein said transesterifying is carried out at a temperature in the range of from 90° C. to 130° C.

13. The process according to claim 1, wherein the temperature at which said transesterifying occurs is increased during the course of the reaction.

14. The process according to claim 12, wherein a temperature at the beginning of said transesterifying is in the range from 90° C. to 110° C. and a temperature at the end of said transesterifying is in the range from 115° C. to 130° C.

15. The process according to claim 1, wherein said transesterifying is carried out in the presence of a polymerization inhibitor.

16. The process according to claim 15, wherein the polymerization inhibitor is an amine.

17. The process according to claim 1, wherein said transesterifying further comprises introducing oxygen to the reaction mixture.

18. The process according to claim 1, further comprising distilling the alcohol liberated from the ester of methacrylic acid to separate the alcohol from the reaction mixture.

19. The process according to claim 18, further comprising separating methanol or ethanol from the reaction mixture.

20. The process according to claim 18, further comprising separating a mixture containing methyl methacrylate and methanol from the reaction mixture.

21. The process according to claim 18, further comprising recirculating the alcohol which has been separated from the reaction mixture into a following batch.

22. The process according to claim 21, wherein the alcohol which is recirculated is obtained at the end of the reaction.

23. The process according to claim 20, further comprising adding methyl methacrylate to the reaction mixture during said transesterifying.

24. The process according to claim 23, wherein the weight ratio of the amount of the methyl methacrylate added to the reaction mixture during said transesterifying to the amount of the mixture containing methyl methacrylate and methanol which is separated is in the range from 2:1 to 1:2.

25. The process according to claim 19, further comprising recirculating the methanol or ethanol which has been separated from the reaction mixture into a following batch.

26. The process according to claim 20, further comprising recirculating the mixture containing methyl methacrylate and methanol which has been separated from the reaction mixture into a following batch.

* * * * *